(12) United States Patent
Bush, Jr. et al.

(10) Patent No.: US 9,241,750 B2
(45) Date of Patent: Jan. 26, 2016

(54) DYNAMIC CERVICAL PLATE

(71) Applicants: Charles L. Bush, Jr., Fairfield, NJ (US); Carla Bandeira, Voorhees, NJ (US)

(72) Inventors: Charles L. Bush, Jr., Fairfield, NJ (US); Carla Bandeira, Voorhees, NJ (US)

(73) Assignee: Stryker Spine (FR)

( * ) Notice: Subject to any disclaimer, the term of this patent is extended or adjusted under 35 U.S.C. 154(b) by 295 days.

(21) Appl. No.: 13/757,226

(22) Filed: Feb. 1, 2013

(65) Prior Publication Data

US 2013/0150897 A1 Jun. 13, 2013

Related U.S. Application Data

(62) Division of application No. 11/900,914, filed on Sep. 13, 2007, now Pat. No. 8,388,663.

(51) Int. Cl.
*A61B 17/80* (2006.01)
*A61B 17/88* (2006.01)
*A61B 17/70* (2006.01)

(52) U.S. Cl.
CPC .............. *A61B 17/88* (2013.01); *A61B 17/7059* (2013.01); *A61B 17/8004* (2013.01); *A61B 17/8023* (2013.01); *A61B 17/8009* (2013.01)

(58) Field of Classification Search
CPC ........... A61B 17/8004; A61B 17/8019; A61B 17/8023; A61B 17/808; A61B 17/7059; A61B 17/8009; A61B 17/8866; A61B 2017/681
USPC .............. 606/246, 257, 280, 70, 71, 281, 282
See application file for complete search history.

(56) References Cited

U.S. PATENT DOCUMENTS

| 3,547,114 A | 12/1970 | Haboush |
| 4,157,715 A | 6/1979 | Westerhoff |
| 4,957,497 A | 9/1990 | Hoogland et al. |

(Continued)

FOREIGN PATENT DOCUMENTS

| EP | 73455 | 3/1983 |
| EP | 181433 | 5/1986 |

(Continued)

OTHER PUBLICATIONS

Chinese Office Action for Application No. 2013-081148 dated Mar. 19, 2014.

(Continued)

*Primary Examiner* — Matthew Lawson
*Assistant Examiner* — Amy Sipp
(74) *Attorney, Agent, or Firm* — Lerner, David, Littenberg, Krumholz & Mentlik, LLP

(57) ABSTRACT

A dynamic subsidence plate is described having a first plate member and a second plate member in sliding engagement that may infinitely subside between a first and second assembled position. The plate includes a lock assembly associated with the first and second plate members. The lock assembly includes a ramp portion, an interference portion, and a bearing member situated between the ramp portion and the interference portion. The lock assembly of the plate is configured to allow movement of the first member with respect to the second member in a first direction in an infinite number of positions between a first assembled position and a second assembled position. Further, the lock assembly alternatively prevents movement of the first member with respect to the second member in an opposite second direction between the first and second assembled positions.

10 Claims, 7 Drawing Sheets

(56) References Cited

U.S. PATENT DOCUMENTS

| | | |
|---|---|---|
| 5,041,113 A | 8/1991 | Biedermann et al. |
| 5,129,903 A | 7/1992 | Luhr et al. |
| 5,616,142 A | 4/1997 | Yuan et al. |
| 5,843,082 A | 12/1998 | Yuan et al. |
| 6,193,720 B1 | 2/2001 | Yuan et al. |
| 6,383,186 B1 | 5/2002 | Michelson |
| 6,402,756 B1 | 6/2002 | Ralph et al. |
| 6,503,250 B2 | 1/2003 | Paul |
| 6,533,786 B1 | 3/2003 | Needham et al. |
| 6,533,787 B1 | 3/2003 | Lenke et al. |
| 6,645,207 B2 | 11/2003 | Dixon et al. |
| 6,666,867 B2 | 12/2003 | Ralph et al. |
| 6,669,700 B1 | 12/2003 | Farris et al. |
| 6,679,883 B2 | 1/2004 | Hawkes et al. |
| 6,689,134 B2 | 2/2004 | Ralph et al. |
| 6,695,846 B2 | 2/2004 | Richelsoph et al. |
| 6,837,905 B1 | 1/2005 | Lieberman |
| 6,872,210 B2 | 3/2005 | Hearn |
| D505,205 S | 5/2005 | Freid |
| 6,890,335 B2 | 5/2005 | Grabowski et al. |
| 6,932,820 B2 | 8/2005 | Osman |
| 6,936,050 B2 | 8/2005 | Michelson |
| 6,964,664 B2 | 11/2005 | Freid et al. |
| 6,969,398 B2 | 11/2005 | Stevens et al. |
| 7,008,427 B2 | 3/2006 | Sevrain |
| 7,214,226 B2 | 5/2007 | Alleyne |
| 2002/0045898 A1 | 4/2002 | Freid et al. |
| 2002/0058939 A1 | 5/2002 | Wagner et al. |
| 2002/0065517 A1 | 5/2002 | Paul |
| 2002/0120273 A1 | 8/2002 | Needham et al. |
| 2002/0128655 A1 | 9/2002 | Michelson |
| 2002/0183756 A1 | 12/2002 | Michelson |
| 2002/0183757 A1 | 12/2002 | Michelson |
| 2002/0188296 A1 | 12/2002 | Michelson |
| 2003/0023242 A1 | 1/2003 | Harrington |
| 2003/0040749 A1 | 2/2003 | Grabowski et al. |
| 2003/0083658 A1 | 5/2003 | Hawkes et al. |
| 2003/0114856 A1 | 6/2003 | Nathanson et al. |
| 2003/0130661 A1 | 7/2003 | Osman |
| 2003/0149434 A1 | 8/2003 | Paul |
| 2003/0187440 A1 | 10/2003 | Richelsoph et al. |
| 2003/0187509 A1 | 10/2003 | Lemole |
| 2003/0212399 A1 | 11/2003 | Dinh et al. |
| 2004/0019353 A1 | 1/2004 | Freid et al. |
| 2004/0030336 A1 | 2/2004 | Khanna |
| 2004/0030338 A1 | 2/2004 | Paul |
| 2004/0068319 A1 | 4/2004 | Cordaro |
| 2004/0087951 A1 | 5/2004 | Khalili |
| 2004/0097934 A1 | 5/2004 | Farris et al. |
| 2004/0097935 A1 | 5/2004 | Richelsoph et al. |
| 2004/0097950 A1 | 5/2004 | Foley et al. |
| 2004/0106924 A1 | 6/2004 | Ralph et al. |
| 2004/0167521 A1 | 8/2004 | De Windt |
| 2004/0181226 A1 | 9/2004 | Michelson |
| 2004/0181229 A1 | 9/2004 | Michelson |
| 2004/0186476 A1 | 9/2004 | Michelson |
| 2004/0220571 A1 | 11/2004 | Assaker et al. |
| 2004/0220572 A1 | 11/2004 | Michelson |
| 2004/0236335 A1 | 11/2004 | Michelson |
| 2004/0260306 A1 | 12/2004 | Fallin et al. |
| 2005/0027297 A1 | 2/2005 | Michelson |
| 2005/0027298 A1 | 2/2005 | Michelson |
| 2005/0033298 A1 | 2/2005 | Hawkes et al. |
| 2005/0043732 A1 | 2/2005 | Dalton |
| 2005/0049593 A1 | 3/2005 | Duong et al. |
| 2005/0059971 A1 | 3/2005 | Michelson |
| 2005/0075633 A1 | 4/2005 | Ross |
| 2005/0137597 A1 | 6/2005 | Butler et al. |
| 2005/0149026 A1 | 7/2005 | Butler et al. |
| 2005/0183756 A1 | 8/2005 | Fang |
| 2005/0187551 A1 | 8/2005 | Orbay et al. |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0192577 A1 | 9/2005 | Mosca et al. |
| 2005/0209593 A1 | 9/2005 | Kolb |
| 2005/0216009 A1 | 9/2005 | Michelson |
| 2005/0216010 A1 | 9/2005 | Michelson |
| 2005/0216011 A1 | 9/2005 | Paul |
| 2005/0234455 A1 | 10/2005 | Binder et al. |
| 2005/0240184 A1 | 10/2005 | Osman |
| 2005/0261689 A1 | 11/2005 | Lin |
| 2005/0261690 A1 | 11/2005 | Binder et al. |
| 2005/0277939 A1 | 12/2005 | Miller |
| 2006/0064097 A1 | 3/2006 | Bray |
| 2006/0074420 A1 | 4/2006 | LeHuec et al. |
| 2006/0079900 A1 | 4/2006 | Mathieu et al. |
| 2006/0100625 A1 | 5/2006 | Ralph et al. |
| 2006/0116683 A1 | 6/2006 | Barrall et al. |
| 2006/0200134 A1 | 9/2006 | Freid et al. |
| 2006/0235398 A1 | 10/2006 | Farris et al. |
| 2007/0185489 A1 | 8/2007 | Abdou |
| 2007/0270964 A1 | 11/2007 | Strohkirch et al. |
| 2008/0119933 A1* | 5/2008 | Aebi et al. ............... 623/17.16 |

FOREIGN PATENT DOCUMENTS

| | | |
|---|---|---|
| EP | 347658 | 12/1989 |
| EP | 374084 | 6/1990 |
| FR | 2634368 | 1/1990 |
| FR | 2697428 | 5/1994 |
| FR | 2728454 A1 | 6/1996 |
| JP | 2001510703 A | 8/2001 |
| JP | 2004530482 A | 10/2004 |
| JP | 2005515823 A | 6/2005 |
| WO | 03063714 | 8/2003 |
| WO | 2006/028971 A1 | 3/2006 |
| WO | 2006/060506 A1 | 6/2006 |
| WO | 2006098908 A1 | 9/2006 |
| WO | 2006107891 A2 | 10/2006 |
| WO | 2007067547 A2 | 6/2007 |
| WO | 200904718 A1 | 1/2009 |

OTHER PUBLICATIONS

DGNC 2003, anterior dynamic stabilization of the middle and lower cervical spine, Dr. Apfelbaum, May 27, 2003.

International Search Report, PCT/US2008/010745, mailed Oct. 8, 2009.

Spinal Concepts Receives FDA Clearance on its SC-AcuFix Ant-Cer Implant, www.spinalconcepts.com, printed Feb. 13, 2006.

Swift Dynamic Anterior Cervical Plate System, DePuy Spine, www.depuyspine.com, printed Feb. 8, 2006.

Vectra, anterior cervical plating system, technique guide, Synthes Spine, 2005.

* cited by examiner

DYNAMIC CERVICAL PLATE

CROSS REFERENCE TO RELATED APPLICATIONS

The present application is a divisional of U.S. patent application Ser. No. 11/900,914, filed Sep. 13, 2007, the disclosure of which is incorporated herein by reference.

FIELD OF THE TECHNOLOGY

The present invention relates to a bone plate, and more particularly it relates to such a dynamic bone plate for use in spine.

BACKGROUND OF THE INVENTION

Spinal fixation plates can be used for a variety of conditions, including for example, providing added strength and rigidity after fusion of adjacent vertebral bodies for securing vertebrae together where an intervening vertebral body has been removed and replaced. Generally, a spinal fixation plate is applied to the anterior side of affected vertebrae to span at least one affected disc space. For example, a spinal fixation plate may be applied to adjacent vertebral bodies where at least a portion of a disc has been removed and a spinal fusion spacer has been inserted.

Generally, a spinal plate may be attached to the anterior of two or more vertebral bodies for the purpose of immobilizing, stabilizing, and/or aligning those vertebrae. Additionally, such a plate may be used, for example, to supplement the function of an intervertebral spacer or artificial disc, to prevent an intervertebral spacer from being expelled from an intervertebral disc space and/or to act as a support for biocompatible bone graft material that is implanted in the disc space.

Orthopedic fixation devices such as spinal plates may be coupled to bone with fasteners inserted through openings in the plates. The fasteners may or may not be secured to the plate. It is known to secure such fasteners to a bone plate, for example, through the use of threads on the fastener and matching threads on the plate, though other means of securement are available. Such a screw-plate interface may decrease the incidence of loosening of the fixation assembly postoperatively. It is also known that a bushing may preferably be disposed in each plate hole to receive the fastener to permit polyaxial movement so that the fastener may be angulated at a surgeon-selected angle. While polyaxial movement of fasteners through set plate hole locations may increase attachment alternatives of the fasteners themselves, the plate holes remain fixed in relation to each other and to the longitudinal axis of the plate. Consequently, undesirable loads may be imposed on the plate fasteners as vertebral bodies subside after a spacer and/or bone graft material is implanted in the intervertebral disc space of adjacent vertebrae.

Further, screw blocking systems are generally provided in a bone plate to keep the fasteners from backing out of the plate. In the present invention, each opening in the plate preferably has a groove or recess for receiving a split ring, though any other suitable screw locking systems may be used in connection with the present invention.

Split rings may be pre-assembled to the bone plate. A split-ring can be sized to expand upon insertion of a bone screw into an opening in the bone plate. Once the head of the screw has passed through the split ring, the split ring can contract under its natural spring tension. When the ring relaxes to its unexpanded state, it prevents the bone screw from backing out of the plate by the engagement of an undersurface of the split-ring and an upwardly facing surface on the bone screw. U.S. Pat. No. 6,602,255, titled "BONE SCREW RETAINING SYSTEM" and issued on Aug. 5, 2003 and U.S. Pat. No. 6,261,291, titled "Orthopedic Implant Assembly" and issued on Jul. 17, 2001, both disclose devices used for securing bone screws to a bone plate and are incorporated herein by reference in their entirety as if fully set forth herein.

Generally, after implanting the spacer between a pair of vertebrae, there is a compression of the spacer between the adjacent vertebral bodies. This compression ensures a good engagement between the spacer and the endplates, increasing the chances that fusion will occur. Often, particularly in the period immediately following surgery, the spacer may subside slightly into the endplates. In the case of allograft spacers, the space between the vertebral endplates may decrease due to graft resorption.

Where a rigid fixation plate is used to connect vertebral bodies, this subsidence may tend to shift more of the spinal load to the plate than is desirable. Such load shifting can also occur due to inaccuracies in installing the plate to the vertebrae. In extreme circumstances, this load shifting can result in non-fusion or incomplete fusion between the adjacent vertebral bodies.

It is known in the art to provide a spinal plate which may be adjustable along the longitudinal axis between a plurality of positions. These plates may generally be described as incremental locking plates that are not infinitely adjustable. Such plates only allow for a first plate and a second plate to be assembled in a finite number of fixed positions with respect to one another by a surgeon or through natural subsidence after implantation. Moreover, many of the plates cannot be extended once locked in a fixed position, and this restricts flexibility during surgery and in revisions.

Accordingly, there exists a need for a fixation system having plates susceptible to infinite adjustment between a first and second assembled position. Such a system preferably includes plates that may freely subside in a first direction, while preventing movement of the plates in a second direction, as well as having the ability to unlock so that the plates can move in the second direction if desirable or necessary. Such a plate preferably provides the desired support to the vertebrae to be fused, and allows compression of the vertebrae with respect to at least a portion of the plate, thereby limiting the undesirable effects of load shielding by the plate due to graft subsidence caused by settling or normal forces experienced in the spinal column.

SUMMARY OF THE INVENTION

A first aspect of the present invention is a dynamic subsidence device. In accordance with one embodiment of the present invention, the dynamic subsidence device comprises a first member, a second member contacting the first member, the first and second members being moveable with respect to one another. Preferably, the device further includes a ramp portion on the first member, an interference portion on the second member, and a bearing member situated between the ramp portion of the first member and the interference portion of the second member. Alternatively, the ramp portion may be adapted to the second member, and the interference portion may be adapted to the first member.

Preferably, the bearing member permits movement of the first member with respect to the second member in a first direction in an infinite number of positions between a first assembled position and a second assembled position. Preferably, the bearing member prevents movement of the first member with respect to the second member in a second direction between the first and second assembled positions.

In accordance with one embodiment of this first aspect of the present invention, the ramp portion of the first member is preferably a curved ramp.

In accordance with another embodiment of this first aspect of the present invention, the first member may further include at least one vertical slot. Preferably, the second member further includes at least two apertures, wherein the first and second member are prevented from disengaging when the vertical slot of the first member is situated between the at least two apertures and a pin is placed through the at least two apertures of the second member and the vertical slot of the first member. Alternatively, the second member may include at least one vertical slot and the first member may include at least two apertures wherein the first and second member are prevented from disengaging when the vertical slot of the second member is situated between the at least two apertures and a pin is placed through the at least two apertures of the first member and the vertical slot of the second member.

The function of the vertical slot in the plate system is to aid in limiting the translation of the first and second members with respect to one another between the first and second assembled position. Further, the function of at least one of the at least two apertures in the plate system is to secure the pin member therein. Preferably, the pin is configured to slidably engage the slot of the first or second member. Preferably, the structure of the slot and pin configuration of the plate system functions to add further security to the slidable engagement of the first and second members with respect to one another.

In accordance with yet another embodiment of this first aspect of the present invention, the first member includes at least one opening for receiving a fastener therein for attaching the first member to a vertebral body of the spine. Preferably, the second member further includes at least one opening for receiving a fastener therein for attaching the second member to a vertebral body of the spine. The openings in the first and second members adapted to receive fasteners therein preferably include a groove or recess for receiving a split ring therein. Preferably, each split ring adapted to an opening is configured to prevent a fastener from backing out of the first and second members by the engagement of an undersurface of the split ring and an upwardly facing surface on the fastener.

In accordance with still yet another embodiment of this first aspect of the present invention, the first member may further include a first prong and a second prong, the first prong having a male portion and a receiving portion, the second prong including the ramp portion. The second member may further include a first prong and a second prong, the first prong having a female portion configured to receive the male portion of the first prong of the first member and a guidance portion configured to engage the receiving portion of the first prong of the first member, the second prong of the second member including the interference portion.

In accordance with still yet another embodiment of this first aspect of the present invention, the bearing member is freely seated between the ramp portion and the interference portion of the lock assembly associated with the first and second plate members when the first and second members are in the first assembled position. Further, the bearing member is preferably freely seated between the ramp portion and the interference portion of the lock assembly when the first member is moving with respect to the second member in a first direction. Alternatively, the bearing member preferably locks between the ramp portion and the interference portion of the lock assembly when the first member is moving with respect to the second member in an opposite second direction thereby impeding the translation of the plates in the second direction. Preferably, as soon as the first and second members are impeded by the lock assembly from translating in the second direction, the bearing member may return to the portion of the ramp portion where it is freely seated between the ramp portion and the interference portion. In this position, the bearing member may rotate freely and the first and second members may subside again while moving in the first direction.

In accordance with still yet another embodiment of this first aspect of the present invention, the lock assembly preferably includes a keyhole configured to allow an instrument to enter a space between the ramp portion and the interference portion and hold the bearing member in place, thus releasing the bearing member locked between the ramp portion and the interference portion. Preferably, the instrument is configured to impart a force on the bearing member sufficient to overcome the frictional forces on the bearing member while locked between the ramp portion and the interference portion. Preferably, the instrument is further configured to move the bearing member back towards the deeper part of the ramp portion where the bearing member may freely rotate.

A second aspect of the present invention is a dynamic subsidence plate for the cervical vertebrae of the spine. In accordance with one embodiment of this second aspect, the dynamic subsidence plate comprises a first member having a protruding end including a ramp portion, a second member having a receiving end configured to slidably receive the protruding end of the first member, the receiving end of the second member including an interference portion, and a bearing member situated between the ramp portion of the first member and the interference portion of the second member.

In accordance with this second aspect of the present invention, the bearing member is preferably configured to allow movement of the first member with respect to the second member in a first direction in an infinite number of positions between a first assembled position and a second assembled position. Preferably, the bearing member is further configured to prevent movement of the first member with respect to the second member in an opposite second direction between the first and second assembled positions.

A third aspect of the present invention is a dynamic subsidence plate for the cervical vertebrae of the spine. In accordance with one embodiment of this third aspect, the dynamic subsidence plate comprises a first member having a first prong and a second prong, the first prong having a male portion and a receiving portion, the second prong having a ramp portion. The plate preferably further comprises a second member for receiving the first member, the second member having a first prong and a second prong, the first prong having a female portion configured to receive the male portion of the first prong of the first member and a guidance portion configured to engage the receiving portion of the first prong of the first member, the second prong of the second member having an interference portion. Preferably, the plate further comprises a bearing member freely seated between the ramp portion of the second prong of the first member and the interference portion of the second prong of the second member when the first member is moving with respect to the second member in a first direction and alternatively locked between the ramp portion of the second prong of the first member and the interference portion of the second prong of the second member when the first member is moving with respect to the second member in an opposite second direction.

An exemplary method of providing dynamic subsidence between a first and second body with the plate device of the present invention includes slidably engaging the first and second plate members together and maintaining the first and second plate members in a first assembled position. The method including fastening the first member to the first body and the second member to the second body and allowing the first and second plate members to subside in a first direction in an infinite number of positions between the first assembled position and a second assembled position, wherein the first body and the second body are closer together when the plate device is in the second assembled position.

Preferably, the plate device further includes a lock assembly having a ramp portion, an interference portion, and a bearing member, wherein the bearing member is located in a deeper portion of the ramp portion when the plate device is in the first assembled position. Preferably, the bearing is lodged between the ramp portion and the interference portion of the lock assembly when the plate is in the second assembled position, the bearing preventing the first and second plate members from subsiding further in the first direction.

The method may further include inserting an instrument between the ramp portion and the interference portion such that the instrument may be used to release the lodged bearing.

BRIEF DESCRIPTION OF THE DRAWINGS

A more complete appreciation of the subject matter of the present invention and the various advantages thereof can be realized by reference to the following detailed description in which reference is made to the accompanying drawings in which.

DETAILED DESCRIPTION

Figure 1:
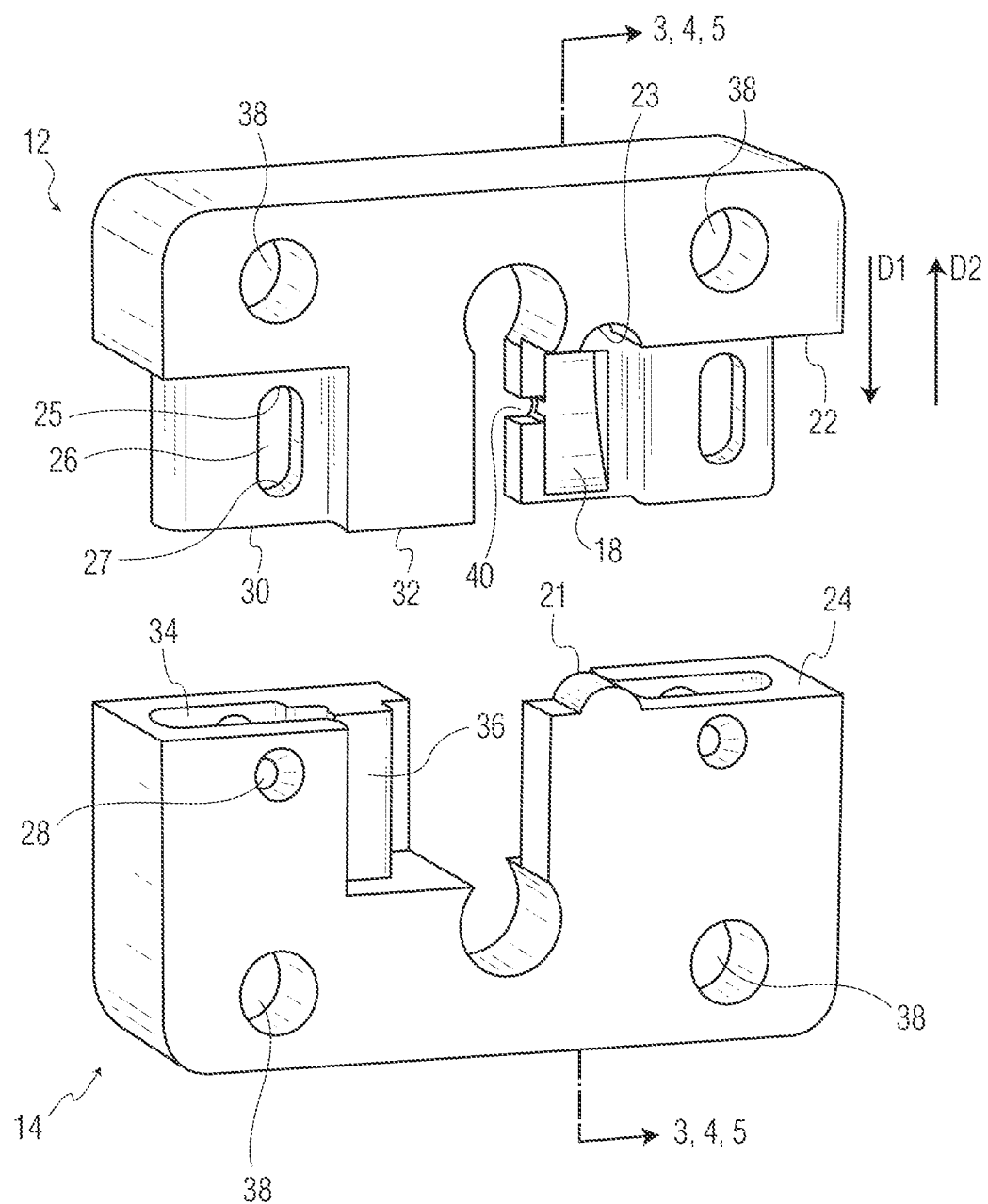
FIG. 1 is an exploded front view of a dynamic subsidence plate according to a first embodiment of the present invention.

As used herein, when referring to bones or other parts of the body, the term "proximal" means closer to the heart and the term "distal" means more distant from the heart. The term "inferior" means lower or bottom and the term "superior" means upper or top. The term "anterior" means towards the front part of the body or the face and the term "posterior" means towards the back of the body. The term "medial" means toward the midline of the body and the term "lateral" means away from the midline of the body.

Referring to the drawings, wherein like reference numerals refer to like elements, there is shown in FIGS. 1-11, an embodiment of the dynamic cervical plate of the present invention designated generally by reference numeral 10. As shown in those figures, plate 10 includes a first plate member 12, a second plate member 14, and a lock assembly 16. Preferably, first member 12 and second member 14 are slidably engagable.

Preferably, lock assembly 16 includes a ramp portion 18 on first member 12, an interference portion 20 on second member 14, and a bearing member 19 situated between ramp portion 18 of first member 12 and interference portion 20 of second member 14. Alternatively, ramp portion 18 may be adapted to second member 14 and interference portion 20 may be adapted to first member 12. Preferably, ramp portion 18 is either an inclined plane or a curved ramp, while it is contemplated ramp portion 18 may be other geometric or non-geometric configurations.

Preferably, lock assembly 16 is configured to allow movement of first member 12 with respect to second member 14 in a first direction in an infinite number of positions between a first assembled position and a second assembled position. Preferably, lock assembly 16 substantially prevents movement of first member 12 with respect to second member 14 in an opposite second direction between the first and second assembled positions.

Preferably, first member 12 includes a mating surface 22 configured to substantially engage a mating surface of second member 14. The sliding engagement of first member 12 and second member 14 in the first direction can no longer occur after surfaces 22, 24 mate.

Preferably, when plate 10 is in the first assembled position, first member 12 and second member 14 are in sliding engagement. Further, bearing member 19 is preferably freely seated between ramp portion 18 and interference portion 20 in the first assembled position. Preferably, a surgeon preoperatively decides the amount of subsidence between first member 12 and second member 14 of plate 10 that is needed for a particular patient.

Depending on the particular patient, plate 10 is generally configured to subside 1 mm to 10 mm. Generally, surface 22 of first member 12 and surface 24 of second member 14 are slidably engaged and distanced approximately 1 mm to 4 mm apart in the first assembled position. A surgeon may decide based on the type of operation performed or the particular patient's anatomy and/or deformity to have surface 22 of first member 12 and surface 24 of second member 14 in the first assembled position at a greater distance than 4 mm. The second assembled position is defined as the position where sliding engagement of first member 12 and second member 14 in the first direction is prevented, generally, after surfaces 24, 26 mate.

In a preferred embodiment, first member 12 may translate freely with respect to second member 14 in a first direction D1 without engaging lock assembly 16. Preferably, lock assembly 16 is configured to allow first member 12 and second member 14 to slide freely with respect to one another in first direction D1. Generally, first direction D1 is a downward direction as surface 22 of first member 12 translates toward second member 14. Movement in the first direction may only occur for first member 12 if second member 14 is in a fixed position. However, because of the anatomical structure and function of the spine, first and second members 12, 14 will generally both translate with respect to one another as subsidence occurs. Therefore, first member 12 and second member 14 both generally define movement in first direction D1 and second direction D2. It is also contemplated that the present invention is applicable to implants other than plates and further, other than plates moving in directly opposite directions.

Figure 9:
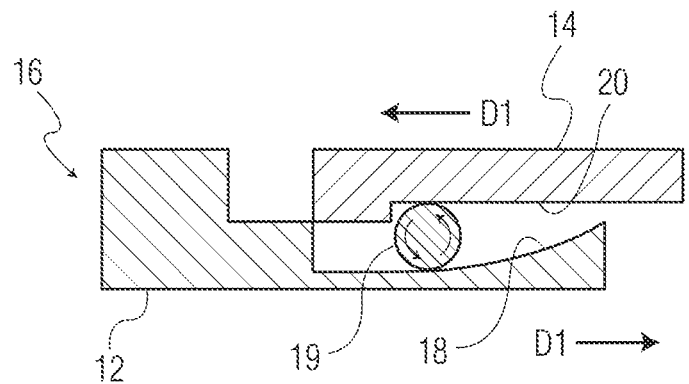
FIG. 9 is a cross-sectional view taken along line 3-3 of the lock assembly of the dynamic subsidence plate of FIG. 1 when the first member and the second member are in an exemplary first assembled position.
Figure 10:
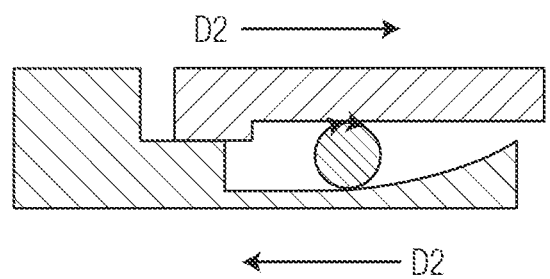
FIG. 10 is a cross-sectional view taken along line 4-4 of the lock assembly of the dynamic subsidence plate of FIG. 1 when the first member and the second member are in a locked position.
Figure 11:
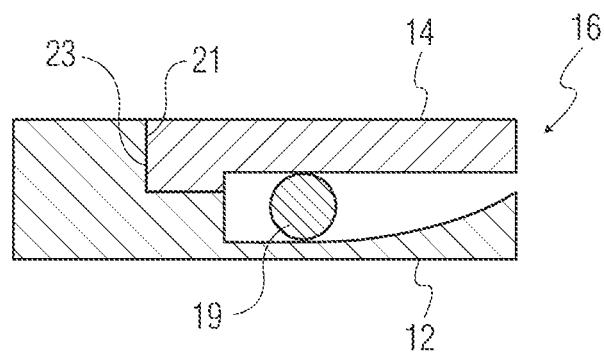
FIG. 11 is a cross-sectional view taken along line 5-5 of the lock assembly of the dynamic subsidence plate of FIG. 1 when the first member and the second member are in an exemplary second assembled position.

As shown in FIGS. 9-11, lock assembly 16 preferably provides a locking mechanism to allow movement or translation of members 12, 14 freely in first direction D1, while preventing backward movement or translation of members 12, 14 in reference to one another in second direction D2. Preferably, bearing member 19 is located in the deeper part of ramp portion 18 when first member 12 and second member 14 are in sliding engagement at an exemplary first assembled or at rest position as shown in FIG. 9.

As first member 12 and second member 14 begin to subside, bearing member 19 is preferably static and will rotate in place in the deeper area of the pocket. As shown in FIG. 10, if first member 12 and second member 14 begin to move or translate in opposite second direction D2 and members 12, 14 therefore start to pull apart, bearing member 19 will be forced to rotate up ramp portion 18 due to the friction created between ramp portion 18 and interference portion 20 of members 12, 14.

Preferably, bearing member 19 will rotate up ramp portion 18 until the amount of point loading of bearing member 19 with respect to ramp portion 18 and interference portion 20 of members 12, 14 is sufficient enough to stop the movement or translation of members 12, 14 in second direction D2. Preferably, this point loading occurs instantaneously as the movement of members 12, 14 change from first direction D1 to second direction D2.

Preferably, movement of members 12, 14 in second direction D2 is less than 1 mm. Preferably, lock assembly 16 is further configured such that if first member 12 and second member 14 have stopped moving apart in direction D2, and start moving towards each other again in direction D1, bearing member 19 may go back down ramp portion 18, thus releasing lock assembly 16.

The depth and shape of ramp portion 18, interference portion 20, and the size of bearing 22 are all critical features for performance and design intent of dynamic plate 10. If the dimensions of ramp portion 18 and interference portion 20 are constant among several different plates, the distance between the first and second assembled positions of plate 10 may be affected by the size of bearing member 19.

Further, the locking forces imparted by ramp portion 18 and interference portion 20 on bearing member 19 may be affected by the size of bearing member 19. One skilled in the art would easily understand that a larger bearing between similarly sized ramp portions 18 and interference portions 20 of different plates 10 would place a greater force on bearing member 19 as well as limit the distance that the plates may translate in the first and/or second directions between the first and second assembled positions.

Figure 12:
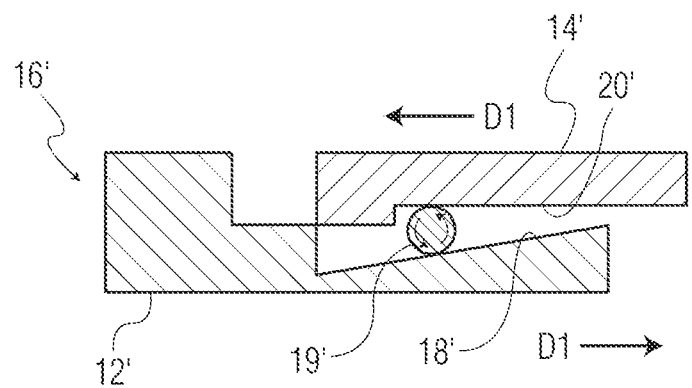
FIG. 12 is a cross-sectional view of an alternative dynamic subsidence plate showing the ramp portion of the lock assembly when the first member and the second member are in an exemplary first assembled position, the ramp portion shown as an inclined plane.
Figure 13:
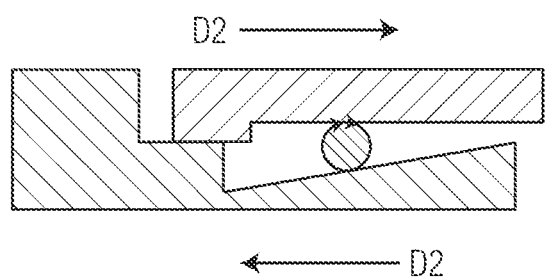
FIG. 13 is a cross-sectional view of the plate of FIG. 12 showing the ramp portion of the lock assembly when the first member and the second member are in a locked position, the ramp portion shown as an inclined plane.
Figure 14:
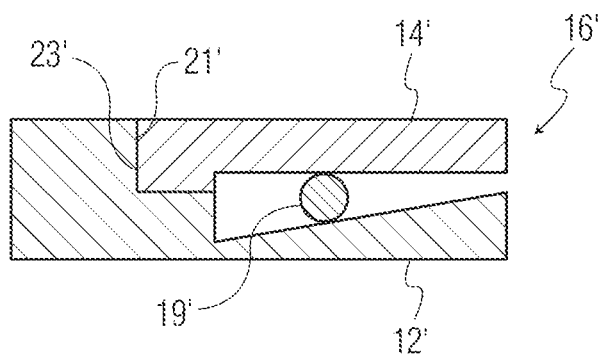
FIG. 14 is a cross-sectional view of the plate of FIG. 12 showing the lock assembly when the first member and the second member are in an exemplary second assembled position, the ramp portion shown as an inclined plane.

FIGS. 12-14 show an alternative embodiment of a lock assembly 16' for a dynamic plate 10'. Preferably, lock assembly 16' includes an inclined plane ramp portion 18'. Lock assembly 16' preferably provides a locking mechanism to allow movement or translation of a plate member 12' and a plate member 14' freely in first direction D1, while preventing backward movement or translation of members 12', 14' in reference to one another in second direction D2. Preferably, bearing member 19' is located in the deeper part of ramp portion 18' when first member 12' and second member 14' are in sliding engagement at an exemplary first assembled or at rest position as shown in FIG. 12.

As first member 12' and second member 14' begin to subside, bearing member 19' is preferably static and will rotate in place in the deeper area of the pocket. As shown in FIG. 13, if first member 12' and second member 14' begin to move or translate in opposite second direction D2 and members 12', 14' therefore start to pull apart, bearing member 19' will be forced to rotate up ramp portion 18' due to the friction created between ramp portion 18' and interference portion 20' of members 12', 14'.

Preferably, bearing member 19' will be forced to rotate up ramp portion 18', until the amount of point loading of bearing member 19' with respect to ramp portion 18' and interference portion 20' of members 12', 14' is sufficient enough to stop the movement or translation of members 12', 14' in second direction D2. Preferably, this point loading occurs instantaneously as the movement of members 12', 14' change from first direction D1 to second direction D2.

Preferably, movement of members 12', 14' in second direction D2 is less than 1 mm. Preferably, lock assembly 16' is further configured such that if first member 12' and second member 14' have stopped moving apart in direction D2, and start moving towards each other again in direction D1, bearing member 19' may go back down ramp portion 18', thus releasing lock assembly 16'.

Figure 2:
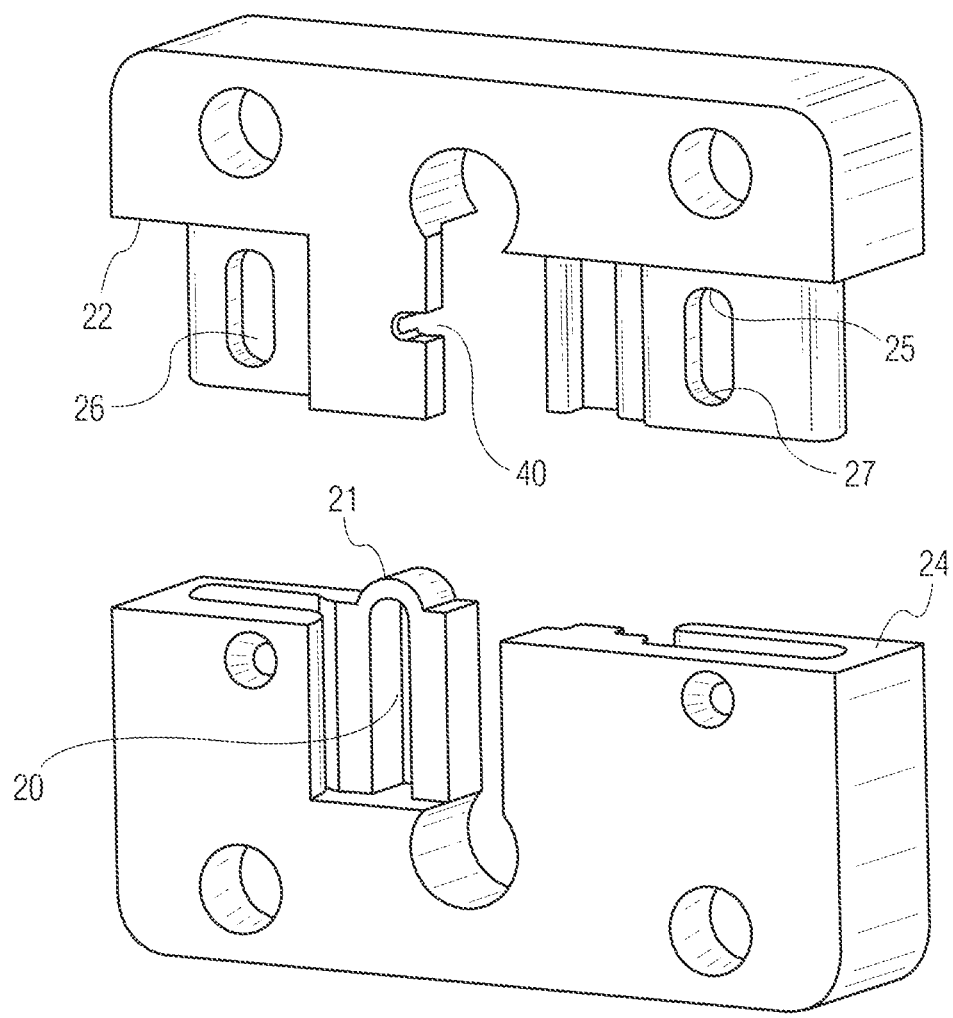
FIG. 2 is an exploded rear view of the dynamic subsidence plate of FIG. 1.

In FIG. 2, an exploded rear view of first member 12 and second member 14 of plate 10 is shown. Interference portion 20 is shown, while ramp portion 18 is now hidden on the other side of first member 18. Preferably, a slight protrusion 21 extends outwardly from interference portion 20. Preferably, first member 12 further includes a recessed portion 23 as shown in FIG. 1. Protrusion 21 is preferably configured to engage recessed portion 23. The engagement of protrusion 21 and recessed portion 23 acts to further secure first member 12 and second member 14 in an exemplary second assembled position as shown in FIG. 11. Further, protrusion and recessed portion 23 may act to guide the sliding engagement of members 12, 14 between the first and second assembled positions.

Figure 5:
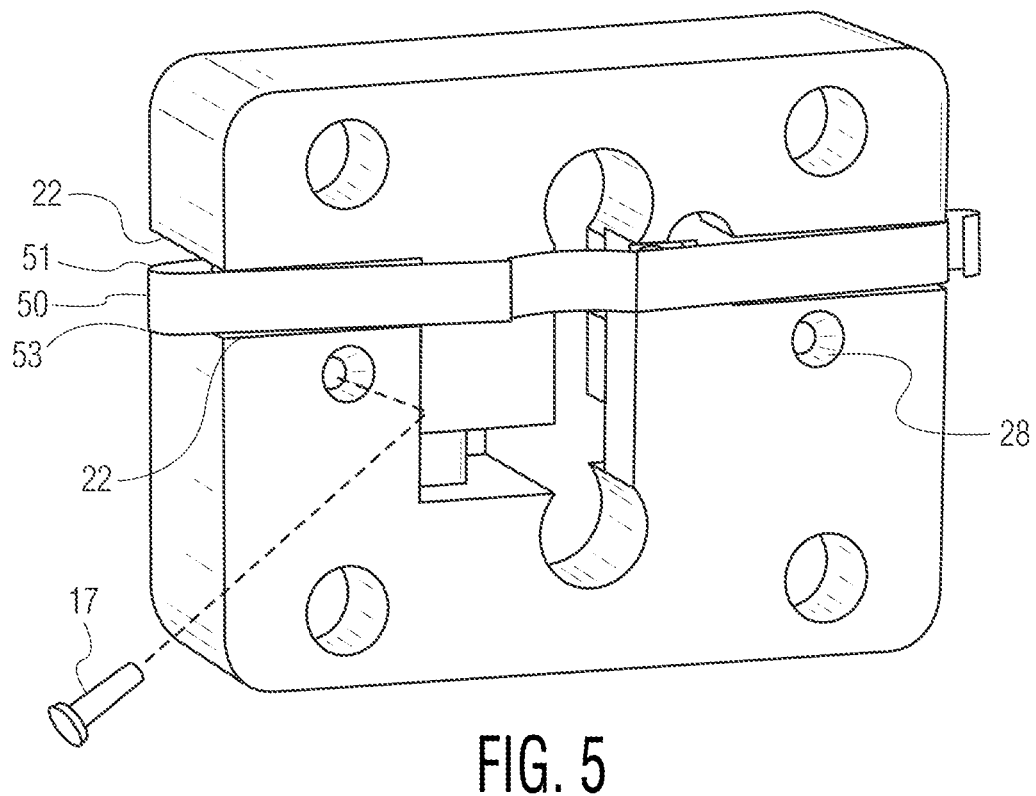
FIG. 5 is a front assembled view of an exemplary embodiment of a first member, a second member, and a clip, the clip used to maintain the first member and the second member in a first assembled position.
Figure 7:
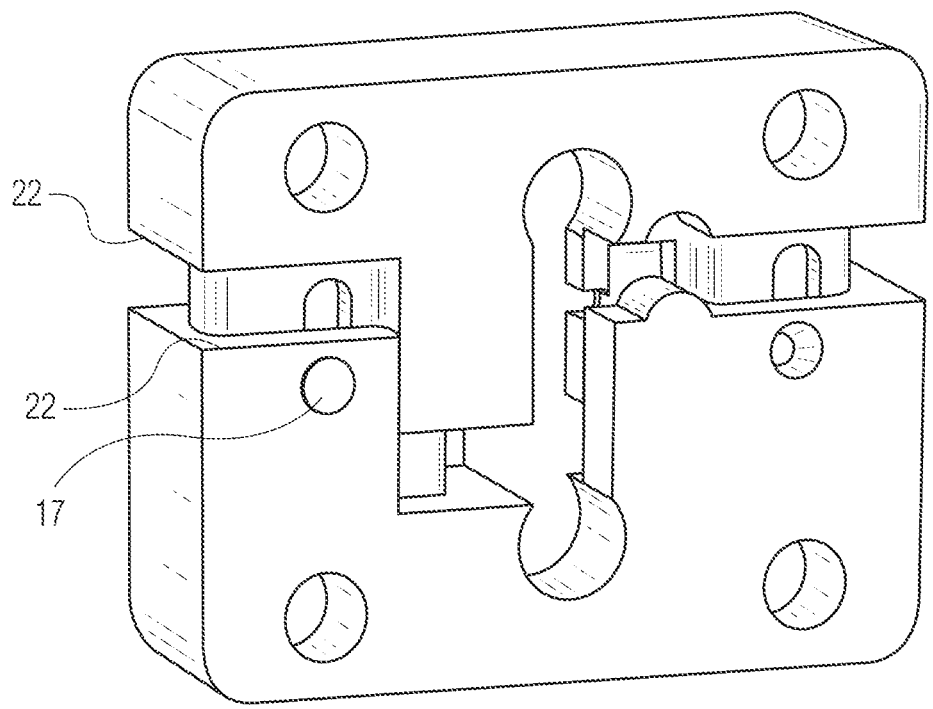
FIG. 7 is a front assembled view of the plate of FIG. 1 showing the vertical slot of the first member situated between the at least two apertures of the second member and a pin placed through the at least two apertures of the second member and the vertical slot of the first member.
Figure 8:
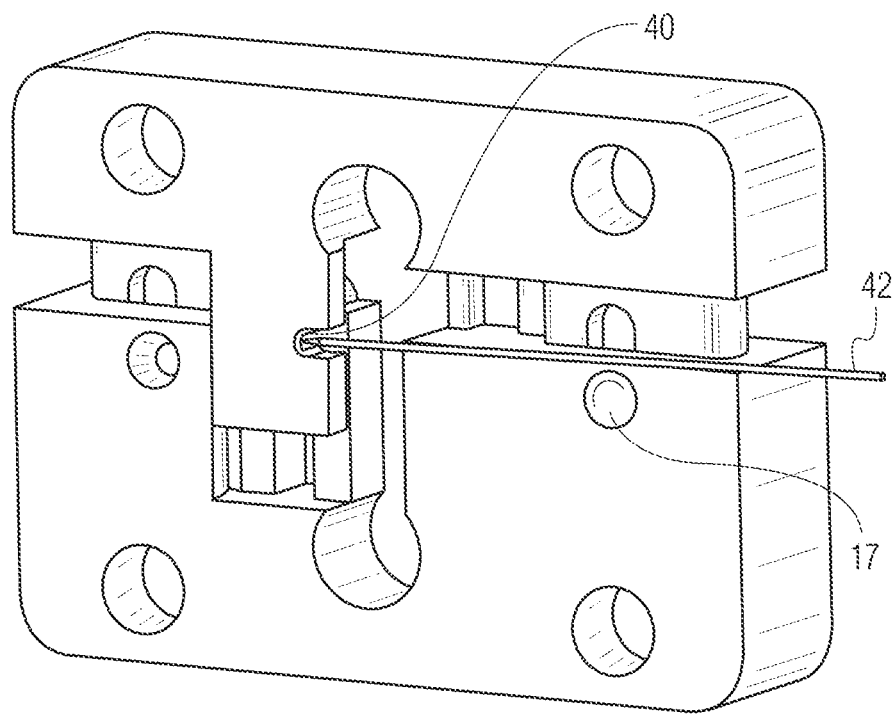
FIG. 8 is a back assembled view of the plate of FIG. 1 showing an instrument inserted into the keyhole of the first member.

In one embodiment, first member 12 further includes at least one vertical slot 26. Preferably, second member 14 further includes at least two apertures 28, wherein first and second member 12, 14 are prevented from disengaging when vertical slot 26 of first member 12 is situated between at least two apertures 28. Further, a pin 17 is preferably placed through at least two apertures 28 of second member 14 and vertical slot 26 of first member 12 as shown for example, in FIGS. 5 and 6. Preferably, pin 17 is a deformable rivet that may be inserted into a first aperture 28 as shown in FIGS. 5 and 7, and later be deformed to engage and be fixed within second aperture 28 as shown in FIG. 8.

Alternatively, second member 14 may include at least one vertical slot 26 and first member 12 may include at least two apertures 28 wherein first and second members 12, 14 are prevented from disengaging when vertical slot 26 of second member 14 is situated between at least two apertures 28. In this alternative embodiment, pin 17 is placed through at least two apertures 28 of first member 12 and vertical slot 26 of second member 14.

Preferably, the function of vertical slot 26 is to aid in limiting the translation of first and second members 12, 14 with respect to one another between the first and second assembled positions. Further, apertures 28 in first and second members 12, 14 preferably act to secure pin 17 therein. Preferably, pin 17 is configured to slidably engage the slot of first and second members 12, 14. Further still, the slot 26 and pin 17 configuration preferably acts to add further security to the slidable engagement of first and second members 12, 14.

Preferably, vertical slot 26 includes a top portion 25 and a bottom portion 27. When the first and second members 12, 14 are in the first assembled position, pin 17 is preferably through slot 26 and apertures 28 and is adjacent to bottom portion 27 of slot 26. Alternatively, when the first and second members 12, 14 are in the second assembled position, pin 17 is preferable through slot 26 and apertures 28 and is adjacent to top portion 25 of slot 26.

Openings 38 in plate 10 for receiving bone screws may be seen in plate 10. Typically, spinal plates are secured to adjacent vertebrae by bone screws which pass through openings in the plates. Screw blocking systems are provided to keep the vertebral screws from backing out of the plate. In the present invention, each opening 38 in members 12, 14 preferably has grooves or recesses for receiving a split ring, though any other suitable screw locking systems may be used.

Plate 10 may further include a keyhole 40 associated with either first and/or second members 12, 14. Preferably, keyhole 40 is configured to allow an instrument 42 to enter at least some of the space between ramp portion 18 and interference portion 20 as shown generally in FIG. 8. Preferably, instrument 42 is configured to dislodge bearing member 19 from between ramp portion 18 and interference portion 20 and/or hold bearing member 19 in place in the deeper portion of ramp portion 18. Instrument 42 may be used to release bearing member 19 locked between ramp portion 18 and interference portion 20.

Preferably, instrument 42 is configured to impart a force on bearing member 19 sufficient to overcome the frictional forces on bearing member 19 while locked between ramp portion 18 and interference portion 20. Preferably, instrument 42 is further configured to move bearing member 19 back towards the deeper part of ramp portion 18 where bearing member 19 may freely rotate as shown in FIG. 9.

Figure 3:
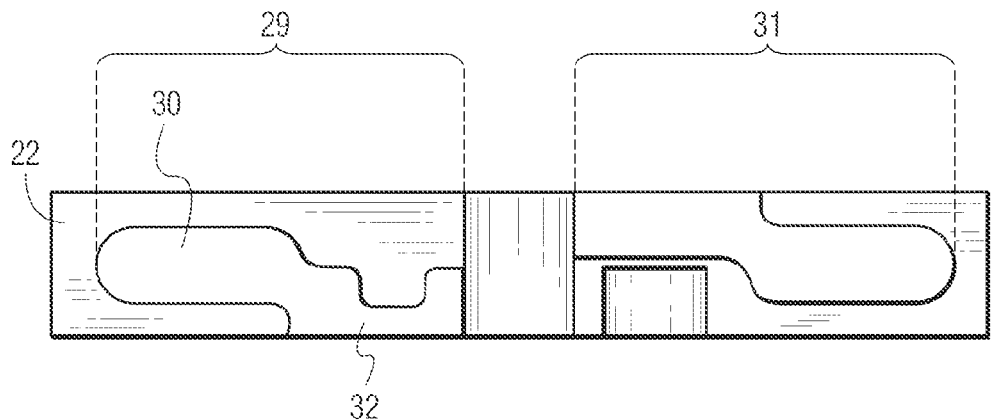
FIG. 3 is a top view of the second member of the dynamic subsidence plate of FIG. 1.
Figure 4:
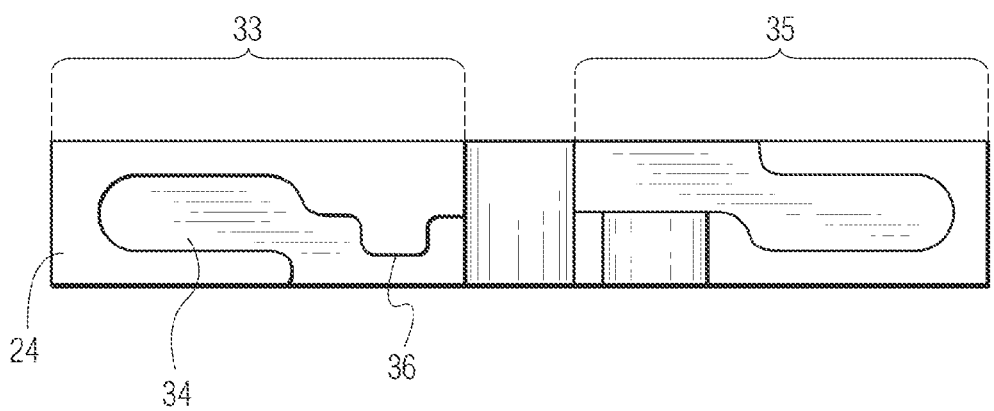
FIG. 4 is a top view of the second member of the dynamic subsidence plate of FIG. 1.

FIGS. 3 and 4 are top views of members 12 and 14 respectively. As shown in FIG. 3, first member 12 preferably includes a first prong 29 and a second prong 31 extending outwardly from surface 22. Preferably, first prong 29 includes a male portion 30 and a receiving portion 32 and second prong 31 includes ramp portion 18. As shown in FIG. 4, second member 14 preferably includes a first prong 33 and a second prong 35. Preferably, first prong 33 includes a female portion 34 and a guidance portion 36. Female portion 34 is preferably configured to receive male portion 30 of first prong 29 of first member 12 and guidance portion 36 is preferably configured to engage receiving portion 32 of first prong 29 of first member 12. Preferably, second prong 35 of second member 14 includes interference portion 20.

FIG. 5 is a view of first and second members 12, 14 of plate 10 in an exemplary first assembled position. Preferably, a clip 50 is used to maintain the spacing between surfaces 22, 24 of first and second members 12, 14 in the first assembled position. Clip 50 preferably includes a top portion 51, a first end 52, a bottom portion 53, and a second end 54. Preferably, in the first assembled position, surface 22 of first member 12 rests on top portion 51 of clip 50 and bottom portion 53 of clip 50 rests on surface 24 of second member 14.

Figure 6:
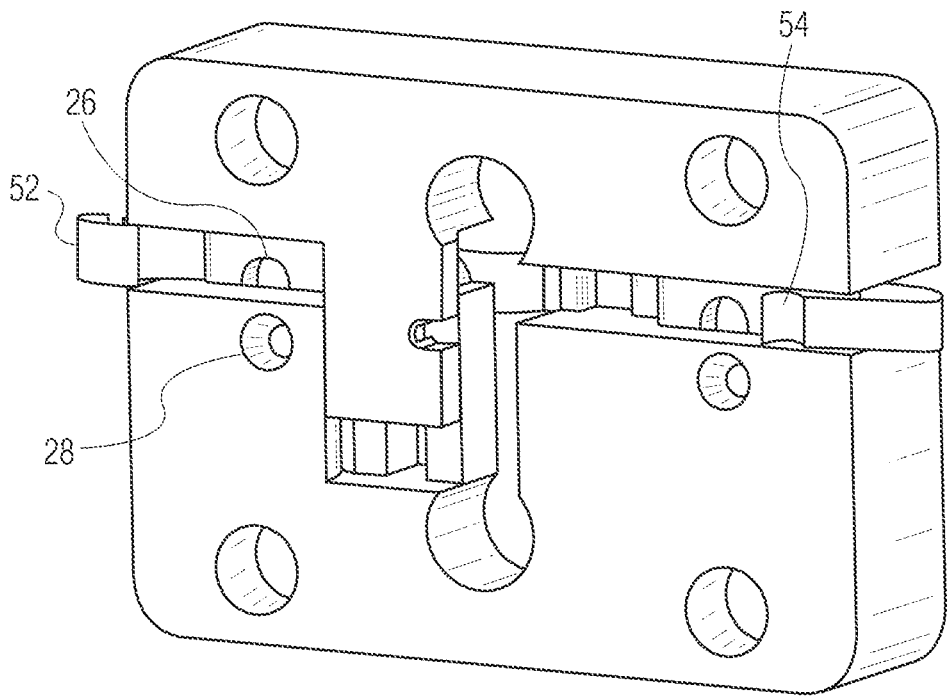
FIG. 6 is a back assembled view of the assembly of FIG. 5.

As shown in FIG. 6, clip 50 may encompass a portion of the perimeter of members 12, 14 such that a surgeon or medical technician has access to ends 52, 54 after members 12, have been implanted. It is preferred, that clip 50 functions to maintain the spacing of members 12, 14 in the first assembled position while also being configured to easily be removed from between members 12, 14. Alternatively, clip may encircle the entire perimeter of members 12, 14. Preferably, clip 50 is made of a material strong enough to withstand forces that may be generated between members 12, 14 before and after implantation of members 12, 14 to a respective vertebral body.

One method of implanting plate 10 includes fastening first and second members 12, 14 in the first assembled position to a respective vertebral body, clip 50 used to maintain members 12, 14 of plate 10 in the first assembled position, and removing clip 50 from the assembly such that first member 12 and second member 14 may translate in a first direction D1. In this exemplary method, plate 10 further includes lock assembly 16 configured to allow first and second members 12, 14 to subside in a first direction in an infinite number of positions between a first assembled position and a second assembled position and alternatively limit the translation of the first member 12 and the second member 14 in an opposite second direction D2.

Behind assembled clip 50 in the first assembled position, bearing member 19 is generally located in the deeper part of ramp portion 18. After clip 50 is removed from between members 12, 14, bearing member 19 is preferably static and will rotate in place in the deeper area of the pocket as surfaces 22, 24 of members 12, 14 slowly come together as natural subsidence occurs. If during subsidence, first member 12 and second member 14 begin to move or translate in second direction D2, bearing member 19 will be forced to rotate up ramp portion 18 due to the friction created between ramp portion 18 and interference portion 20 of members 12, 14.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of providing dynamic subsidence between a first and second body with a plate device having first and second plate members, comprising:
maintaining the first and second plate members in sliding engagement with one another in a first assembled position with a separation member, the separation member having an elongate portion flanked by two curved portions and top and bottom surfaces each in contact with one of corresponding mating surfaces of the first and second plate members, the two curved portions each lying adjacent front and back surfaces of the first and second plate members;

fastening the first plate member to the first body and the second plate member to the second body; and removing the separation member from contacting the first and second plate members to allow the first and second plate members to translate in an infinite number of positions between the first assembled position and a second assembled position, wherein the corresponding mating surfaces of the first and second plate members are separated by a first linear distance when in the first assembled position and a second linear distance when in the second assembled position, the first linear distance being greater than the second linear distance.

2. The method of claim 1, wherein the separation member is a clip member used to maintain the first and second plate members in the first assembled position, the clip being located at least partially between the corresponding mating surfaces of the first and second plate members when the first and second plate members are in the first assembled position.

3. The method of claim 2, wherein top and bottom surfaces of the clip member are each in contact with one of the corresponding mating surfaces of the first and second plate members when the first and second plate members are in the first assembled position.

4. The method of claim 3, wherein the clip member is removed from between the corresponding mating surfaces of the first and second plate members in order to allow the first and second plate members to translate toward one another.

5. The method of claim 3, wherein the clip member has a height measured as a distance between the top and bottom surfaces of the clip member.

6. The method of claim 5, wherein the height of the clip member is the same as the first distance that the corresponding mating surfaces of the first and second plate members are separated by when in the first assembled position.

7. The method of claim 1, wherein the plate device further includes a lock assembly having a ramp portion, an interference portion, and a bearing member, wherein the bearing member is located in a deeper portion of the ramp portion when the plate device is in the first assembled position.

8. The method of claim 7, wherein the bearing member is lodged between the ramp portion and the interference portion of the lock assembly when the plate is in the second assembled position, the bearing member preventing the first and second plate members from translating away from another.

9. The method of claim 8, including inserting an instrument between the ramp portion and the interference portion such that the instrument may be used to release the lodged bearing member.

10. A method of providing dynamic subsidence between a first and second body with a plate device having first and second plate members, comprising:

maintaining the first and second plate members in sliding engagement with one another in a first assembled position with a top surface of a separation member contacting a first mating surface of the first plate member and a bottom surface of the separation member contacting a second mating surface of the second plate member such that the first and second mating surfaces of the first and second plate members are separated from one another by the separation member having a substantially straight portion flanked by two curved portions, the two curved portions each lying adjacent front and back surfaces of the first and second plate members;

fastening the first plate member to the first body and the second plate member to the second body; and removing the separation member from contact with the first and second plate members to allow the first and second plate members to translate in an infinite number of positions between the first assembled position and a second assembled position, wherein the first and second mating surfaces of the first and second plate members are separated by a lesser linear distance when in the second assembled position than when in the first assembled position.

\* \* \* \* \*